US010041929B2

(12) United States Patent
Just et al.

(10) Patent No.: US 10,041,929 B2
(45) Date of Patent: Aug. 7, 2018

(54) METHOD FOR CONTROLLING ELECTRODES FOR BIO-IMPEDANCE MEASUREMENTS AND APPARATUS FOR BIO-IMPEDANCE MEASUREMENTS

(75) Inventors: Marcin Pawel Just, Wroclaw (PL); Michal Hugo Tyc, Wroclaw (PL); Przemyslaw Los, Zurawice (PL)

(73) Assignee: BONE VITAE SA, Warsaw (PL)

( * ) Notice: Subject to any disclaimer, the term of this patent is extended or adjusted under 35 U.S.C. 154(b) by 985 days.

(21) Appl. No.: 14/382,267

(22) PCT Filed: Mar. 29, 2012

(86) PCT No.: PCT/IB2012/051529
§ 371 (c)(1),
(2), (4) Date: Feb. 20, 2015

(87) PCT Pub. No.: WO2013/128243
PCT Pub. Date: Sep. 6, 2013

(65) Prior Publication Data
US 2015/0160185 A1 Jun. 11, 2015

(30) Foreign Application Priority Data
Feb. 29, 2012 (PL) .......................................... 398277

(51) Int. Cl.
*G01N 27/02* (2006.01)
*A61B 5/00* (2006.01)
(Continued)

(52) U.S. Cl.
CPC ......... *G01N 33/4833* (2013.01); *A61B 5/053* (2013.01); *A61B 5/4504* (2013.01);
(Continued)

(58) Field of Classification Search
CPC .................. A61B 5/053–5/0538; G01N 27/02
(Continued)

(56) References Cited

U.S. PATENT DOCUMENTS 5,174,303 A * 12/1992 Schroeppel ............ A61N 1/056
600/364
5,272,624 A 12/1993 Gisser
(Continued)

FOREIGN PATENT DOCUMENTS

GB 2449226 11/2006
PL 390500 8/2011
(Continued)

OTHER PUBLICATIONS

Aidan Doyle, ISR and Written Opinion of International Searching Authority, dated Nov. 15, 2012, PCT/IB2012/051529.
(Continued)

*Primary Examiner* — Michael C Stout
(74) *Attorney, Agent, or Firm* — Nexsen Pruet, LLC; John B. Hardaway, III

(57) ABSTRACT

Method for Controlling Electrodes for Bio-impedance Measurements and Apparatus for Bio-impedance Measurements There is provided a control circuit for electrodes in a bio-impedance measurement system, the bio-impedance measurement system comprising screening current injecting electrodes and measuring current injecting electrodes, the control circuit comprising: a current generator for connection to at least one screening current injecting electrode; and an measuring signal output configured to establish a measuring potential between the measuring current injecting electrodes, wherein the control circuit is configured such that the measuring potential is dependent on a measure of a potential difference resulting from the screening current. The control circuit uses the value of the potential resulting from the screening current to determine the potential difference between the measuring current injecting electrodes. In this way the flow of measuring current can be made smaller than the screening current and necessarily at a safe level.

13 Claims, 5 Drawing Sheets

(51) Int. Cl.
*G01N 33/483* (2006.01)
*A61B 5/053* (2006.01)

(52) U.S. Cl.
CPC .......... *A61B 5/4509* (2013.01); *A61B 5/6824* (2013.01); *G01N 27/02* (2013.01)

(58) Field of Classification Search
USPC ............................................................ 600/547
See application file for complete search history.

(56) References Cited

U.S. PATENT DOCUMENTS

| | | | | |
|---|---|---|---|---|
| 5,454,377 | A * | 10/1995 | Dzwonczyk | A61B 5/0535 600/547 |
| 5,782,763 | A | 7/1998 | Bianco et al. | |
| 5,836,876 | A | 11/1998 | Dimarogonas | |
| 6,631,292 | B1 | 10/2003 | Liedtke | |
| 2004/0054298 | A1 | 3/2004 | Masuo et al. | |
| 2005/0203434 | A1 * | 9/2005 | Kassab | A61B 5/02007 600/547 |
| 2006/0253174 | A1 * | 11/2006 | King | A61N 1/36185 607/62 |
| 2007/0043303 | A1 * | 2/2007 | Osypka | A61B 5/0535 600/547 |
| 2007/0179390 | A1 * | 8/2007 | Schecter | A61B 5/053 600/508 |
| 2008/0221477 | A1 * | 9/2008 | Olson | A61B 5/053 600/547 |
| 2008/0300504 | A1 * | 12/2008 | Lefkov | A61B 5/053 600/547 |
| 2009/0326600 | A1 * | 12/2009 | Kracker | A61N 1/3706 607/27 |
| 2010/0030293 | A1 * | 2/2010 | Sarkar | A61B 5/046 607/18 |
| 2010/0198097 | A1 * | 8/2010 | Sowelam | A61B 5/0245 600/538 |
| 2011/0087085 | A1 * | 4/2011 | Tsampazis | A61B 5/053 600/379 |
| 2011/0137199 | A1 | 6/2011 | Karo | |
| 2011/0264171 | A1 * | 10/2011 | Torgerson | A61N 1/36 607/59 |
| 2012/0209135 | A1 * | 8/2012 | Zdeblick | A61B 5/0537 600/547 |
| 2015/0258341 | A1 * | 9/2015 | Ternes | A61N 1/36142 607/17 |

FOREIGN PATENT DOCUMENTS

| | | |
|---|---|---|
| WO | 2011102743 | 8/2011 |
| WO | WO2011/102743 | 8/2011 |

OTHER PUBLICATIONS

Arthur Kogul, Polish Search Report for P.398277, dated Mar. 28, 2012.

Cecile Chatel, International Preliminary Report on Patentability, dated Sep. 2, 2014, PCT/IB2012/051529.

Doyle, ISR and Written Opinion of International Searching Authority, PCT/IB2012/051529.

* cited by examiner

METHOD FOR CONTROLLING ELECTRODES FOR BIO-IMPEDANCE MEASUREMENTS AND APPARATUS FOR BIO-IMPEDANCE MEASUREMENTS

FIELD OF THE INVENTION

The present invention relates to a method for controlling electrodes in a bio-impedance measurement apparatus and a control circuit for electrodes in a bio-impedance measurement apparatus. In particular, the invention relates to a method and control circuit that allows for a plurality of different bio-impedance measurement methods to be used by simply changing the configuration of the connection of the electrodes.

BACKGROUND TO THE INVENTION

Bio-impedance measurement techniques are known in the art. Bio-impedance measurement consists of passing a known current through tissues and measuring the resulting potential difference. Bio-impedance measurements can be used to determine a variety of properties of the tissue under investigation, for example for determining the structure of bone tissue.

To obtain accurate and useful results, it is essential to measure the potentials appearing across the tissues under investigation and not the potential across the tissues which surround the investigated ones, and to ensure that as much as possible of the measuring current flows through the investigated tissue. To achieve this, in the most frequently used configuration, separate electrodes are used to inject measuring current and to measure the resulting potential difference. This method is known as the four-electrode method and it eliminates the influence of contact resistances of measurement electrodes.

When parasitic current flows through tissues which are not under investigation it can create significant problems, resulting in loss of accuracy and reliability of the output measurements. A method of applying a dynamically generated, additional screening potential to the tissues has been proposed, which can greatly reduce undesired current flows. Such a method, using 6 to 8 electrodes, is described in international patent application No. PCT/PL2011/000014, entitled "Method and Apparatus for Non-invasive Analysing the Structure and Chemical Composition of Bone Tissue Eliminating the Influence of Surrounding Tissues." The purpose of the electronic circuit controlling the electrodes is to generate a measuring current that is both adequate and safe, to measure the resulting potential, and—in the case when a dynamic screening potential is applied—to generate an additional screening potential. As the number of measurement electrodes grows, the complexity level of the control circuit, and the number of pins in the connector between the control circuit and the electrodes, grows as well, but the measurement capabilities of the entire apparatus are increased.

The measurement method described in the above mentioned patent application, in its most sophisticated form, requires 8 measurement electrodes. It consists in conducting measurements as in the classical four-electrode method, with the difference that the value of measured potential is monitored and the value of screening potential is dynamically adjusted so that the undesired current flows are minimized. The screening potential results from the flow of screening current, which typically reach values greater than the measuring current, and in extreme cases may be much greater than the measuring current. Such a method of current control requires that the very low level of measuring current intensity is applied, so that the larger screening current does not exceed the safety threshold defined by medical devices safety regulations. However, the use of too low a measuring current, decreases the signal to noise ratio and lowers the sensitivity of the apparatus. This makes implementing the measurement method difficult in practice.

It is an object of the invention to provide an alternative bio-impedance measurement method and control circuit that allows for greater control over the screening current and measurement current levels. It is also an object of the invention to provide a control circuit that allows for the possibility of changing the measurement configuration by simply changing the connection of electrodes to the control circuit.

SUMMARY OF THE INVENTION

The invention is defined in the appended claims, to which reference should be made.

In one embodiment, there is provided a method of controlling signals applied to electrodes in a bio-impedance measurement system, the bio-impedance measurement system comprising screening current injecting electrodes and measuring current injecting electrodes for application to a subject under test, comprising: applying a constant amplitude screening current to the screening current injecting electrodes, measuring a potential difference resulting from the screening current, and establishing a measuring potential between the measuring current injecting electrodes based on the potential difference resulting from the screening current, wherein a measuring current resulting from the measuring potential is smaller than the screening current, and wherein the measuring current and a potential associated with the measuring current are used to determine characteristics of the subject under test.

The screening current reduces the flow of measuring current through the tissues surrounding the tissue under investigation. It is advantageous that the amplitude of screening current is fixed at a constant and safe level, and that it determines the potential difference between the measuring current injecting electrodes, ensuring that the flow of measuring current remains at a safe level, without activating additional protection circuits and is typically smaller than screening current.

The step of establishing a measuring potential may comprise maintaining and regulating dynamically the measuring potential at a level proportional to the potential difference resulting from the screening current.

The step of measuring a potential difference resulting from the screening current may comprise measuring the potential between the screening current injection electrodes or between a separate pair of probe electrodes forming part of the bio-impedance measurement system.

In another embodiment of the invention, there is provided a control circuit for electrodes in a bio-impedance measurement system, the bio-impedance measurement system comprising screening current injecting electrodes and measuring current injecting electrodes, the control circuit comprising:
 a current generator, driven by a voltage generator, for connection to at least one screening current injecting electrode;
 a screening potential input configured to receive a measure of a potential difference resulting from the screening current; and an measuring signal output configured to establish a measuring potential between the measuring current injecting electrodes, wherein the control circuit is configured such that the measuring potential is dependent on the measure of a potential difference resulting from the screening current.

The screening current reduces the flow of measuring current through the tissues surrounding the tissue under investigation. It is advantageous that the amplitude of screening current is fixed at a constant and safe level, and that the control circuit uses the value of the potential resulting from the screening current to determine the potential difference between the measuring current injecting electrodes. In this way the flow of measuring current is typically smaller than screening current and necessarily at a safe level, without activating additional protection circuits.

The measuring current is not directly selected by the operator, but determined by the measuring potential. Because of the anatomic structure of a forearm, it is generally guaranteed to be smaller than the screening current; typically, it is smaller by an order of magnitude. The device may have additional built-in protection against currents (both for screening and measuring currents) rising above the safe level, which is 1000 for this class of devices. However, activation of this protection mechanism introduces measurement errors, so it is desirable to establish the exact amplitude of the screening current and, because of the structure of a forearm, to be subsequently almost certain that the measurement current is smaller. If it is the measurement current that is first established at safe level, the screening current will typically be greater and could easily activate the protection circuits and introduce errors. The protection, in its simplest form, is a series current-limiting resistor.

The control circuit may further comprise an amplifier, wherein an input to the amplifier is connected to the screening potential input and an output is the measuring signal output. The amplifier may be an operational amplifier. The use of operational amplifiers provides a reliable and inexpensive way to design a control circuit that ensures that the measuring potential is proportional to measure of a potential difference resulting from the screening current, and that the measuring current is smaller than the screening current. The control circuit may further comprise a double difference amplifier measuring potentials at test resistors, connected to a measurement output providing a voltage signal proportional to the value of the measuring current. The control circuit may further comprise a difference amplifier measuring the potential difference resulting from the measuring current, connected to a measurement output providing a signal proportional to the value of this difference.

The control circuit may further comprise a measurement input for connection to measurement electrodes, wherein, in use, a signal received by the measurement input is the measure of a potential difference resulting from the measurement current.

The voltage generator may be configured to generate a variable frequency alternating voltage.

The control circuit may comprise a measurement socket for connection to current injection electrodes and measurement electrodes, and an output socket or sockets, wherein the output socket or sockets output a potential produced by the current resulting from the measuring potential or the measuring potential, and the potential proportional to measuring current. In one embodiment, the measurement socket has 10 pins. The output socket may have two pins and is configured for connection to a system which analyzes the amplitude ratio and phase difference of measurement potential and measuring current by means of synchronous detection.

Advantageously, the control circuit is configured to allow different configurations of electrodes to be connected to the measurement socket. In one embodiment, the control circuit is arranged in such a way that a change in configuration of measurement electrodes connected to the pins in the measurement socket is realized simply by changing the connection of the electrodes to the pins of the measurement socket and by shorting selected pins of the measurement socked together or to the ground of the electrode control circuit. Alternatively, or in addition, the measurement socket may include mechanical or semiconductor switches to allow different configurations of electrodes to be connected to the measurement socket.

It is advantageous that the connection of one of the measurement electrodes remains unchanged between the different configurations of electrodes, so that it can be electrically fixed to the respective point in the control circuit, bypassing the measurement socket, which allows integration of this electrode with the apparatus casing.

It is advantageous that asymmetrical configuration of measurement electrodes can be applied, which limits the number of measurement electrodes to 6 or 5, while the full capabilities of the circuit, with elimination of parasitic currents, are retained.

In another embodiment, there is provided a bio-impedance measurement system comprising a control circuit in accordance with any of the embodiments described above and a device configured to analyze the amplitude ratio and phase difference of a potential produced by the current resulting from the measuring potential or the measuring potential, and the current resulting from the measuring potential.

As will be appreciated, a method, control circuit and bio-impedance measurement system in accordance with the present invention eliminates the danger of inappropriate choice of measuring current value in the measurement method with elimination of parasitic currents, when either the corresponding screening current exceeds the limits imposed by safety regulations, or the measuring current is too low causing increased noise. The amplitude of the screening current is maintained at constant level, according to medical devices safety regulations, and the measurement electrodes are dynamically controlled with specialized electronic circuit realizing feedback function and ensuring optimum measurement conditions, i.e., minimizing the parasitic current flow through tissues irrelevant from the diagnostic point of view.

Another advantage of the invention consists in its compatibility with less advanced measurement methods, such as a two-electrode method and a four-electrode method, allowing for a common measurement module operable with each configuration of measurement electrodes. The cost of manufacturing different versions of an apparatus is lowered, as a single apparatus can work with different sets of measurement cables corresponding to different measurement methods. When the common measurement module is intended for use with the less developed electrode sets, further cost lowering is possible by not soldering the elements unnecessary for those methods onto the common printed circuit board of the control circuit.

Another advantage of the invention consists in the increased stability of the control circuit related to the fact, that after the screening potential is established, the changes in measuring current influence the screening potential to minimal extent. In the opposite case, when the measurement potential is established initially, the secondary change in the screening potential substantially influences the magnitudes of the measuring current and the measurement potential resulting from its flow.

BRIEF DESCRIPTION OF THE DRAWINGS

Examples of the present invention will now be described, by way of example only, with reference to the accompanying drawings, in which.

DETAILED DESCRIPTION

Figure 1:
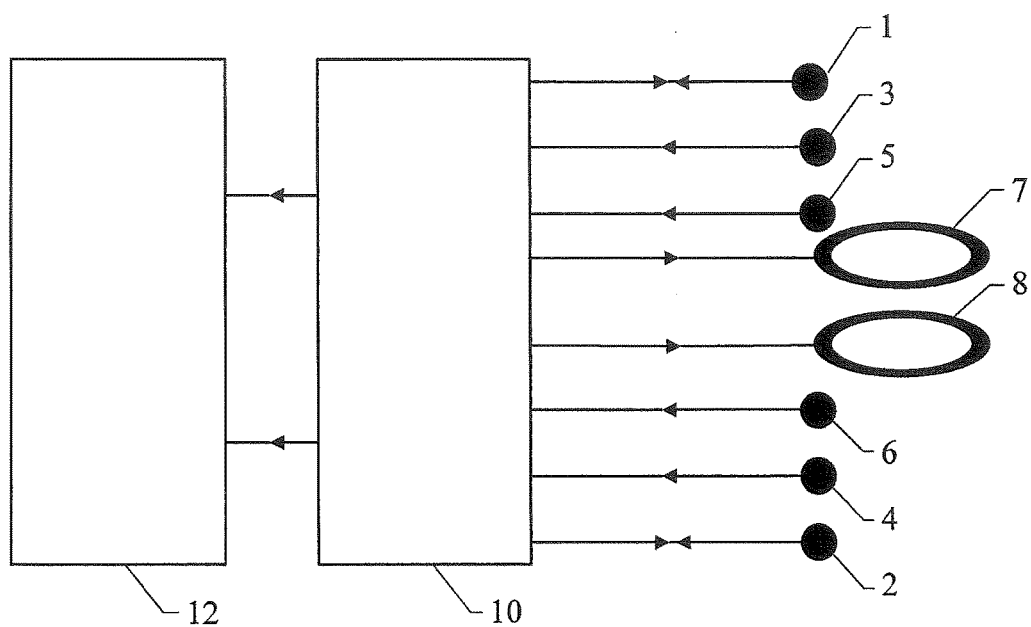
FIG. 1 is a schematic diagram of a bio-impedance measurement apparatus incorporating a control circuit in accordance with the present invention.

FIG. 1 shows a general schematic representation of a bio-impedance measurement apparatus incorporating a control circuit in accordance with the present invention. The bio-impedance measurement system comprises a control circuit 10 connected to electrodes 1 to 8, and to an analysis device 12. The analysis device may be a suitably programmed general purpose computer or may include hardware designed specifically for the purpose. The analysis device may be integrated with the control circuit 10 on a single printed circuit board. The purpose of the analysis device is to provide an output meaningful to an end user from the measured potential and current from the control circuit. Devices of this type are known in the art of phase-sensitive signal measurement and it is not necessary to describe it in detail here. The analysis may be performed with any two-channel, two-phase lock-in amplifier (such as Scitec Instruments' 450DV2 or Anfatec Instruments' eLockIn204/2) connected to a PC.

Figure 2:
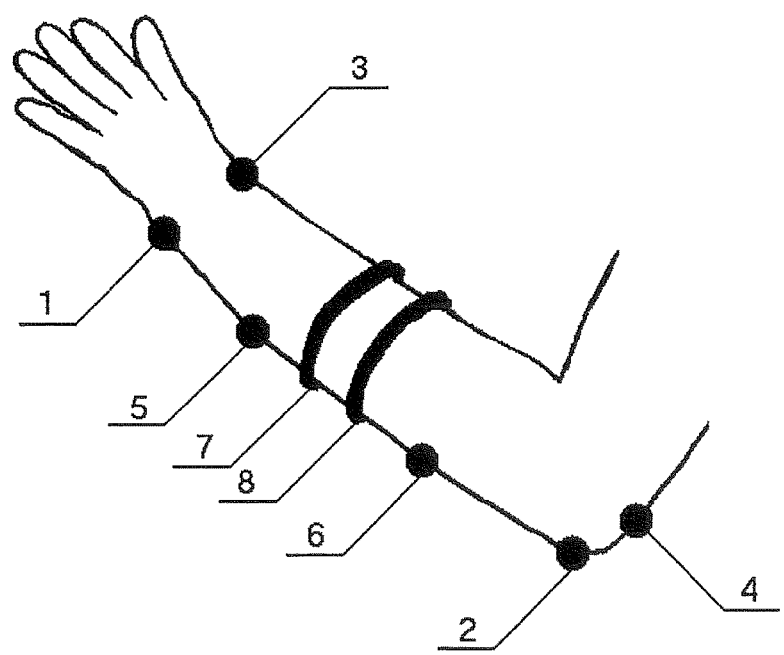
FIG. 2 is a schematic illustration of the electrodes of the system of FIG. 1 positioned on a forearm of a subject.

FIG. 2 shows an example placement of the electrodes on the forearm of a subject. Electrodes 1 and 2 are used to apply a measuring current to the bone. Electrodes 3 and 4 are used to measure the potential resulting from the measuring current. The measuring current and the resulting potential measured by electrodes 3 and 4, or signal derived from these, are provided as the output to the analysis circuit. Electrodes 7 and 8 are used to apply a screening current to the tissues surrounding the bone under investigation. The screening current ensures that the measuring current is largely restricted to the bone under investigation rather than the surrounding tissues. Electrodes 5 and 6, referred to herein as probe electrodes, are used to measure the potential resulting from the screening current. The signals from electrodes 5 and 6 are used to control the magnitude of the measuring current.

Figure 3:
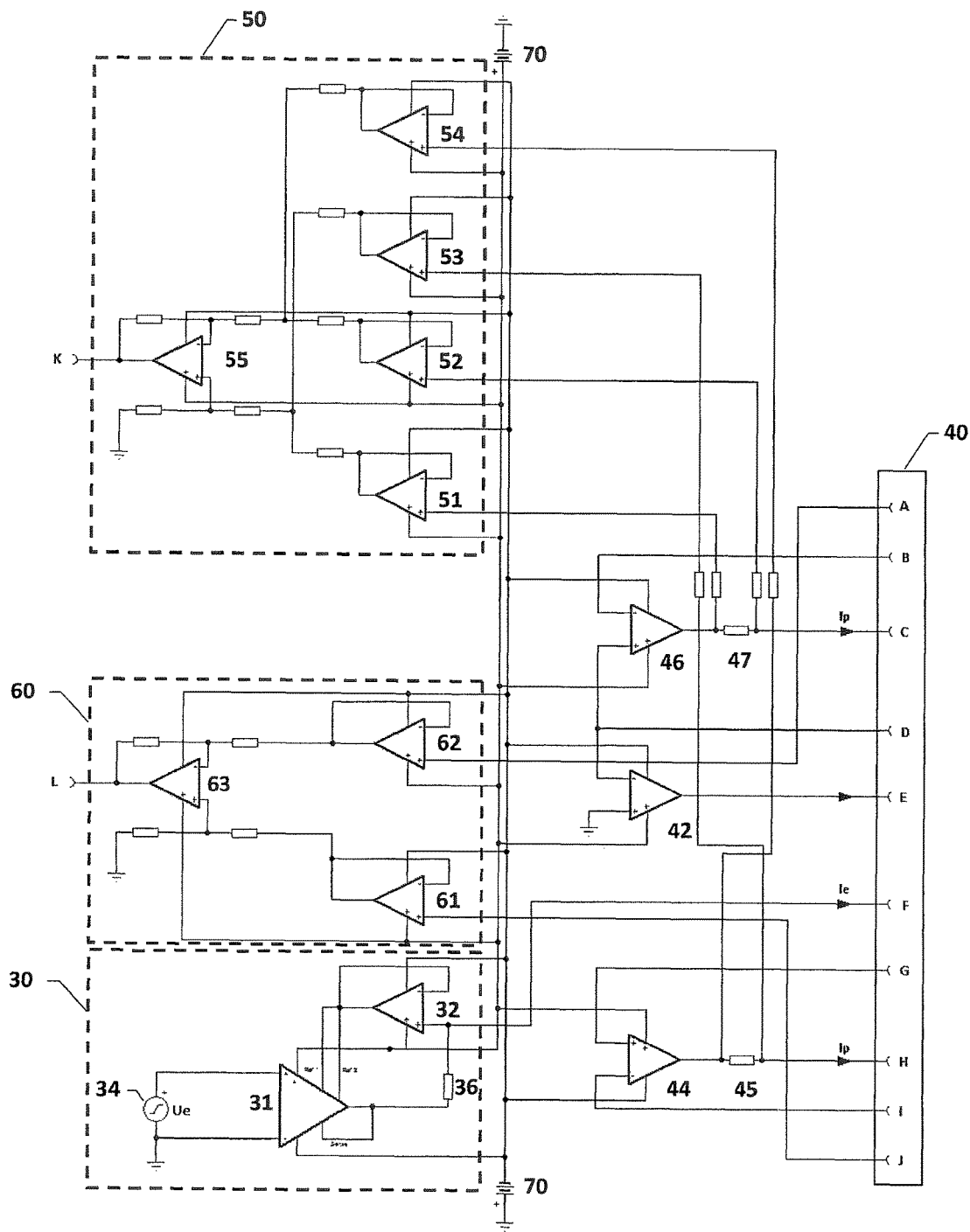
FIG. 3 illustrates an example of a control circuit on accordance with the present invention.

FIG. 3 illustrates one example of a control circuit 10 in accordance with the present invention. The control circuit comprises a screening current generator 30, consisting of the digital voltage generator 34 driving a current source which consists of the differential amplifier 31 and the separation amplifier 32. The screening current $I_e$, which depends on the values of the voltage from the voltage generator 34 and the precision resistor 36, is output to the pin F of the measurement socket 40. The screening current $I_e$ is received through the operational amplifier 42 which keeps the potential at the pin D of the measurement socket 40 on its inverting input very close to the ground potential on its non-inverting input by adjusting the potential at its output connected to the pin E; after connecting to the measured object, then pins D and E are connected together by object's resistance and the pin E works as virtual ground which can absorb current from the pin F.

The operational amplifiers 44 and 46 generate measuring current at the pins H and C of the measurement socket 40, respectively. A double difference amplifier 50 consisting of the operational amplifiers 51, 52, 53, 54, 55 measures potentials at the test resistors 45 and 47 and provides at the measurement output K a voltage signal proportional to the value of the measuring current $I_p$.

A difference amplifier 60 consisting of the operational amplifiers 61, 62, 63 measures the potential difference between the input pins A and J of the measurement socket 40, and provides at measurement output L a signal proportional to the value of this difference.

The voltage sources 70 supply symmetric ±2.5 V power to all operational amplifiers. The value of the voltages supplied can be chosen to suit the range of resistances to be measured. In this embodiment, the maximum resistances are of the order of 10 kΩ. Advantageously, there is a variety of CMOS operational amplifiers available in the market with supply voltages in the ±1.65 V to ±2.75 V range. Although a non-symmetric supply voltages are possible, a symmetric supply is desirable as it does not produce any additional DC components in the screening and measurement currents.

To additionally protect against exceeding 500 μA current flow defined by safety regulations in case of single fault, the resistors 36, 45 and 47 should have values of at least 5 kΩ. To keep the both screening and measurement current below the 100 μA level defined by the safety regulations for normal operation, the voltage at the output of voltage generator 34 should not exceed 500 mV when the differential gain of the amplifier 31 is set to unity.

The screening current injecting electrodes 7 and 8 are connected to the pins E and F of the measurement socket 40, respectively. The measuring current injecting electrodes 1 and 2 are connected to the pins C and H, respectively. The probe electrodes 5 and 6 are connected to the pins D and G, respectively. The electrode 3 measuring the potential produced by the measuring current flow is connected to the pins A and B, and the electrode 4 measuring the potential produced by the measuring current flow is connected to the pins I and J. This way, the full 8-electrode measurement configuration is realized.

The control circuit operates in such a way that the distribution of screening potential in the tissue surrounding the investigated bone is established, and the measuring potential causing the flow of the measuring current $I_p$ is adjusted accordingly, minimizing parasitic currents flow. The screening field is generated in the surrounding tissue by injection of screening current $I_e$ of a magnitude according to medical devices safety regulations, generated in a generator consisting of the digital alternating voltage source 34 and the current source controlled by this voltage. The current source consists of the differential amplifier 31 connected with a precision resistor 36, which sets the value of the current, and a separation amplifier 32, as described above.

Depending on the way the measurement electrodes are connected, without any changes to the electrical scheme of the control circuit, different measurement configurations can be set up: classical two-electrode, classical four-electrode, six-electrode with dynamical screening, eight-electrode with dynamical screening, and asymmetric five-electrode with dynamical screening. The connection schemes for different measurement configurations are shown in FIGS. 4, 5, 6, 7, and 8.

It should be clear to a person of ordinary skill that alternative configurations for the control circuit are possible. Alternative control circuits typically include analogous functional blocks, but have some differences within the blocks. For example, the amplifier 42 might generate a true virtual ground, by connecting its inverting input directly to its output (E) not to D (D will be connected only to non-inverting input of 46). The pin E can be connected directly to ground, and 42 completely removed, too. Current generator 30 can also be constructed in a different way.

The screening current generator is advantageously able to both source current to the load and sink current from the load, while one of the load terminals is connected to ground. Because of these constraints, the use of a Howland current source or a modification of a Howland current source is advantageous. The original Howland source with single operational amplifier is relatively difficult in use because four matched precision resistors are needed to control the current. The modification of the Howland source, shown in FIG. 3, is easier in application. It comprises two operational amplifiers, but only one precision resistor is needed. It should be clear that other modifications of the Howland current source can be used as well.

In a first embodiment in accordance with the invention a method for controlling electrodes for bio-impedance measurements comprises generating an alternating screening current $I_e$ of a magnitude in accordance with safety regulations for medical devices, and applying that screening current to the tissues surrounding the analysed bone by the screening current injecting electrodes 7, 8. The electrodes 1, 2, 5, 6, 7, 8 are positioned on a forearm of the subject as shown in FIG. 2. The screening current electrodes 7, 8 are positioned between the measuring current injecting electrodes 1, 2. The screening potential in the tissues surrounding the bone is measured with the probe electrodes 5, 6, with elimination of the influence of the contact resistances. At the same time, an alternating potential is established at the measuring current injecting electrodes 1, 2, which forces the measuring current flow $I_p$ through the analysed bone. The value of the measuring potential is regulated dynamically and maintained at a level proportional to the potential measured at the probe electrodes 5, 6. The injected measuring current frequency is changed nine times in equal intervals in the range from 250 Hz to 250 kHz during a measurement. The potential at the measuring current injecting electrodes 1, 2, as well as a phase difference between the measuring current injecting electrodes 1, 2 and the measuring current $I_p$ are measured for each of ten injected measuring current frequencies. On the basis of measured electrical values, the structure and chemical composition of bone tissue are evaluated.

In an alternative embodiment in accordance with the invention a method for controlling electrodes for bio-impedance measurements is carried out as in the first embodiment with the difference that the potential produced by the measuring current $I_p$ flow is measured with the electrodes measuring the potential produced by the measuring current flow 3, 4, and the potential at the measuring current injecting electrodes 1, 2 is regulated at a level such that the potential at the probe electrode 5 is equal to the potential at the electrode measuring the potential produced by the measuring current flow 3, and the potential at the probe electrode 6 is equal to the potential at the electrode measuring the potential produced by the measuring current flow 4. The electrodes 1, 2, 3, 4, 5, 6, 7, 8 are positioned on a forearm of the subject as shown in FIG. 2.

A circuit as described in FIG. 3 can be used with varying numbers of electrodes, giving it great flexibility. Examples of different possible connections of the circuit described with reference to FIG. 3 to the electrodes will now be described.

Example 1

Figure 4:
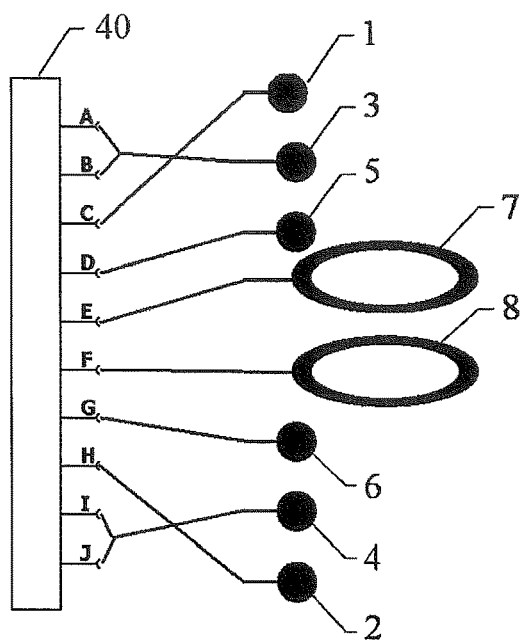
FIG. 4 shows the connection of electrodes to the control circuit of FIG. 3 in accordance with a first configuration.

In a first example the control circuit for electrodes for bio-impedance measurements is as shown in FIG. 3 and comprises a screening current generator 30, consisting of the digital voltage generator 34 driving a current source which consists of the differential amplifier 31 and the separation amplifier 32. The screening current $I_e$, depends on the values of the voltage $U_e$ and the precision resistor 36, and is output to the pin F of the measurement socket 40. The screening current $I_e$ is received through the amplifier 42 which generates potential at the pin E of the measurement socket 40 in such a way that potential at the pin D is equal to the ground potential. The amplifiers 44 and 46 generate measuring current at the pins H and C of the measurement socket 40, respectively. A double difference amplifier 50 consisting of the operational amplifiers 51, 52, 53, 54, 55 measures potentials at the test resistors 45 and 47, and provides at the measurement output K a voltage signal proportional to the value of the measuring current $I_p$. A difference amplifier 60 consisting of the operational amplifiers 61, 62, 63 measures the potential difference between the input pins A and J of the measurement socket 40, and provides at measurement output L a signal proportional to the value of this difference. The connection of electrodes is shown in FIG. 4. The screening current injecting electrodes 7 and 8 are connected to the pins E and F of the measurement socket 40, respectively. The measuring current injecting electrodes 1 and 2 are connected to the pins C and H, respectively. The probe electrodes 5 and 6 are connected to the pins D and G, respectively. The electrode measuring the potential produced by the measuring current flow 3 is connected to the pins A and B, and the electrode measuring the potential produced by the measuring current flow 4 is connected to the pins I and J. This way, the full 8-electrode measurement configuration with dynamic screening is realized.

Example 2

Figure 5:
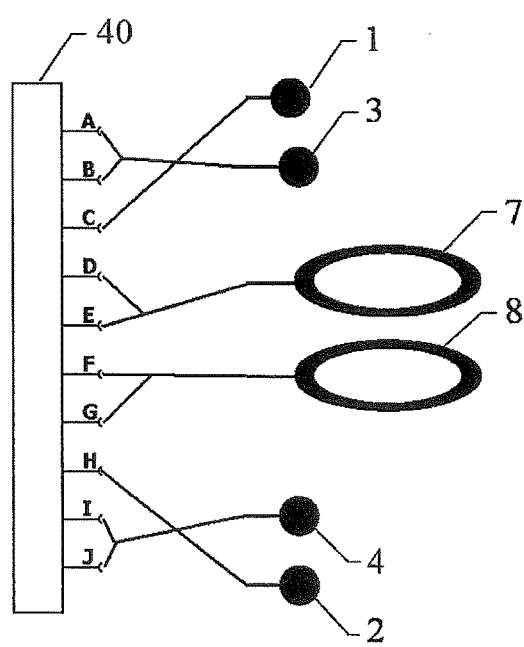
FIG. 5 shows the connection of electrodes to the control circuit of FIG. 3 in accordance with a second configuration.

In a second example, the control circuit is the same as in Example 1 but only the measuring current injecting electrodes 1, 2, the electrodes measuring the potential produced by the measuring current flow 3, 4, and the screening current injecting electrodes 7, 8 are used. The connection of electrodes is shown in FIG. 5. The screening current injecting electrode 7 is connected to the pins D and E of the measurement socket 40. The screening current injecting electrode 8 is connected to the pins F and G. The measuring current injecting electrodes 1 and 2 are connected to the pins C and H, respectively. The electrode measuring the potential produced by the measuring current flow 3 is connected to the pins A and B. The electrode measuring the potential produced by the measuring current flow 4 is connected to the pins I and J. This way, the symmetric 6-electrode configuration of measurements with dynamic screening is realized.

Example 3

Figure 6:
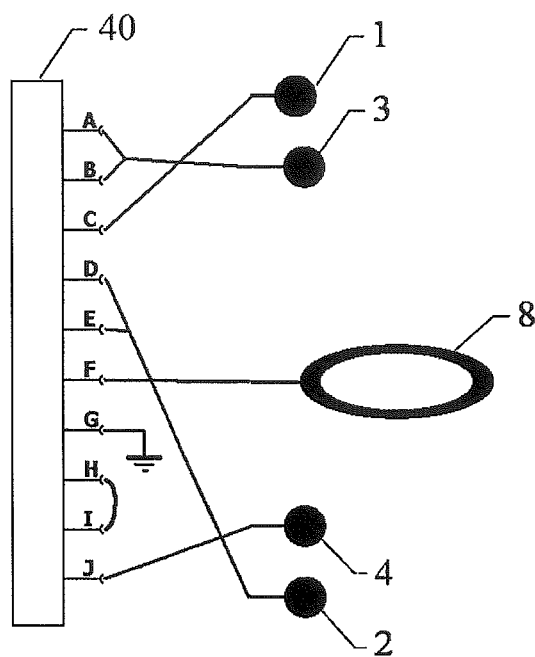
FIG. 6 shows the connection of electrodes to the control circuit of FIG. 3 in accordance with a third configuration.

In a third example, the control circuit is the same as in the Example 1 but only the measuring current injecting electrodes 1, 2, the electrodes measuring the potential produced by the measuring current flow 3, 4, and the screening current injecting electrode 8 are used. The connection of electrodes is shown in FIG. 6. The screening current injecting electrode 8 is connected to the pin F of the measurement socket 40. The measuring current injecting electrode 1 is connected to the pin C. The measuring current injecting electrode 2, which in this configuration injects also the screening current $I_e$, is connected to the pins D and E. The electrode measuring the potential produced by the measuring current flow 3 is connected to the pins A and B. The electrode measuring the potential produced by the measuring current flow 4 is connected to the pin J. The pins I and H are short to each other, and the pin G is short to the ground of the circuit. This way, the simplest 5-electrode configuration of measurements with dynamic screening is realized.

Example 4

Figure 7:
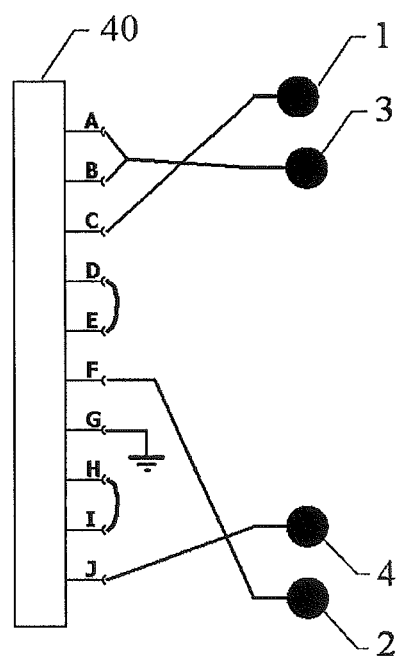
FIG. 7 shows the connection of electrodes to the control circuit of FIG. 3 in accordance with a fourth configuration.

In a fourth example, the control circuit is the same as in the Example 1 but only the measuring current injecting electrodes 1, 2 and the electrodes measuring the potential produced by the measuring current flow 3, 4 are used. The connection of electrodes is shown in FIG. 7. The measuring current injecting electrode 1 is connected to the pin C of the measurement socket 40. The measuring current injecting electrode 2 is connected to the pin F. The electrode measuring the potential produced by the measuring current flow 3 is connected to the pins A and B. The electrode measuring the potential produced by the measuring current flow 4 is connected to the pin J. The pins D and E are short to each other, the pins I and H are short to each other, and the pin G is short to the ground of the circuit. This way, the classic 4-electrode measurements configuration is realized.

Example 5

Figure 8:
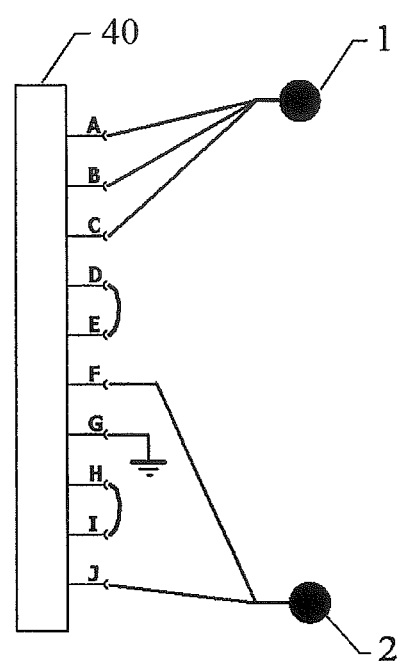
FIG. 8 shows the connection of electrodes to the control circuit of FIG. 3 in accordance with a fifth configuration.

In a fifth example the control circuit is the same as in the Example 4 but only the measuring current injecting electrodes 1, 2 are used. The connection of electrodes is shown in FIG. 8. The measuring current injecting electrode 1 is connected to the pins A, B and C of the measurement socket 40. The measuring current injecting electrode 2 is connected to the pins F and J. The pins D and E are short to each other, the pins I and H are short to each other, and the pin G is short to the ground of the circuit. This way, the classic 2-electrode measurements configuration is realized.

Although in the described examples the electrodes are each separable from the sockets of the control circuit, it should be clear that it is possible to have one or all of the electrodes fixed to the control circuit. For example, the measuring current injecting electrode 1 may be electrically fixed to the output of the control circuit 10, connected to the pin C of the measurement socket 40. At least one electrode may be integrated with the apparatus casing.

The invention claimed is:

1. A method of controlling signals applied to electrodes in a bio-impedance measurement system, the bio-impedance measurement system comprising screening current injecting electrodes and measuring current injecting electrodes for application to a subject under test, comprising: applying a constant amplitude screening current to the screening current injecting electrodes, measuring a potential difference resulting from the screening current, and establishing a measuring potential between the measuring current injecting electrodes based on the potential difference resulting from the screening current, wherein the step of establishing a measuring potential comprises maintaining and regulating dynamically the measuring potential at a level proportional to the potential difference resulting from the screening current, wherein a measuring current resulting from the measuring potential is smaller than the screening current, and wherein the measuring current and a potential associated with the measuring current are used to determine characteristics of the subject under test.

2. A method according to claim 1, wherein the step of measuring a potential difference resulting from the screening current comprises measuring the potential between the screening current injection electrodes or between a separate pair of probe electrodes forming part of the bio-impedance measurement system.

3. A control circuit for electrodes in a bio-impedance measurement system, the bio-impedance measurement system comprising screening current injecting electrodes and measuring current injecting electrodes, the control circuit comprising:
   a current generator, driven by a voltage generator, for connection to at least one screening current injecting electrode;
   a screening potential input configured to receive a measure of a potential difference resulting from the screening current; and
   an measuring signal output configured to establish a measuring potential between the measuring current injecting electrodes, wherein the control circuit is configured such that the measuring potential is dependent on the measure of a potential difference resulting from the screening current, and wherein control circuit is configured to ensure that the measuring potential is proportional to measure of a potential difference resulting from the screening current.

4. A control circuit according to claim 3, further comprising an amplifier, wherein an input to the amplifier is connected to the screening potential input and an output is the measuring signal output.

5. A control circuit according to claim 4, wherein the amplifier is an operational amplifier.

6. A control circuit according to claim 3, configured such that a current resulting from the measuring potential is less that the screening current.

7. A control circuit according to claim 3, wherein the control circuit further comprises a measurement input for connection to measurement electrodes, wherein, in use, a signal received by the measurement input is the measure of a potential difference resulting from the measurement current.

8. A control circuit according to claim 3, wherein the voltage generator is configured to generate a variable frequency alternating voltage.

9. A control circuit according to claim 3, having a measurement socket for connection to current injection electrodes and measurement electrodes, and an output socket or sockets, wherein the output socket or sockets output a potential produced by the current resulting from the measuring potential or the measuring potential, and the potential proportional to measuring current.

10. A control circuit according to claim 9, wherein the control circuit is configured to allow different configurations of electrodes to be connected to the measurement socket.

11. A circuit according to claim 10, wherein the measurement socket includes mechanical or semiconductor switches to allow different configurations of electrodes to be connected to the measurement socket.

12. A bio-impedance measurement system comprising a control circuit in accordance with claim 3 and a device configured to analyze the amplitude ratio and phase difference of a potential produced by the current resulting from the measuring potential or the measuring potential, and the current resulting from the measuring potential.

13. A control circuit for electrodes in a bio-impedance measurement system, the bio-impedance measurement system comprising screening current injecting electrodes and measuring current injecting electrodes, the control circuit comprising:
  a current generator, driven by a voltage generator, for connection to at least one screening current injecting electrode;
  a screening potential input configured to receive a measure of a potential difference resulting from the screening current;
  an measuring signal output configured to establish a measuring potential between the measuring current injecting electrodes, wherein the control circuit is configured such that the measuring potential is dependent on the measure of a potential difference resulting from the screening current; and
  a measurement socket for connection to the current injection electrodes and measurement electrodes, and an output socket or sockets, wherein the output socket or sockets output a potential produced by the current resulting from the measuring potential or the measuring potential, and the potential proportional to measuring current, wherein the control circuit is configured to allow different configurations of electrodes to be connected to the measurement socket, and wherein the measurement socket includes mechanical or semiconductor switches to allow different configurations of electrodes to be connected to the measurement socket.

* * * * *